United States Patent [19]

Hammond et al.

[11] 4,272,269
[45] Jun. 9, 1981

[54] CRYOGENIC EXPANDER RECOVERY PROCESS

[75] Inventors: James D. Hammond; EH Deng, both of Irvine, Calif.

[73] Assignee: Fluor Corporation, Irvine, Calif.

[21] Appl. No.: 96,662

[22] Filed: Nov. 23, 1979

[51] Int. Cl.³ ............................................. F25J 3/02
[52] U.S. Cl. .......................................... 62/17; 62/38; 62/28; 55/57
[58] Field of Search ................... 62/17, 38, 39, 24, 28; 55/57

[56] References Cited

U.S. PATENT DOCUMENTS

| | | | |
|---|---|---|---|
| 4,012,212 | 3/1977 | Kniel | 62/28 |
| 4,061,481 | 12/1977 | Campbell et al. | 62/28 |
| 4,065,278 | 12/1977 | Newton | 62/28 |

*Primary Examiner*—Norman Yudkoff
*Attorney, Agent, or Firm*—Lyon & Lyon

[57] ABSTRACT

A process is described for the separation and recovery of $C_3$ and heavier hydrocarbons from a gaseous hydrocarbon containing feed stream such as natural gas or refinery gas in which the gaseous feed stream is cryogenically expanded and the expanded gas is brought into contact with an absorption medium. The $C_3$ and heavier components are liquefied and subsequently subjected to distillation and recovered as liquid product.

12 Claims, 1 Drawing Figure

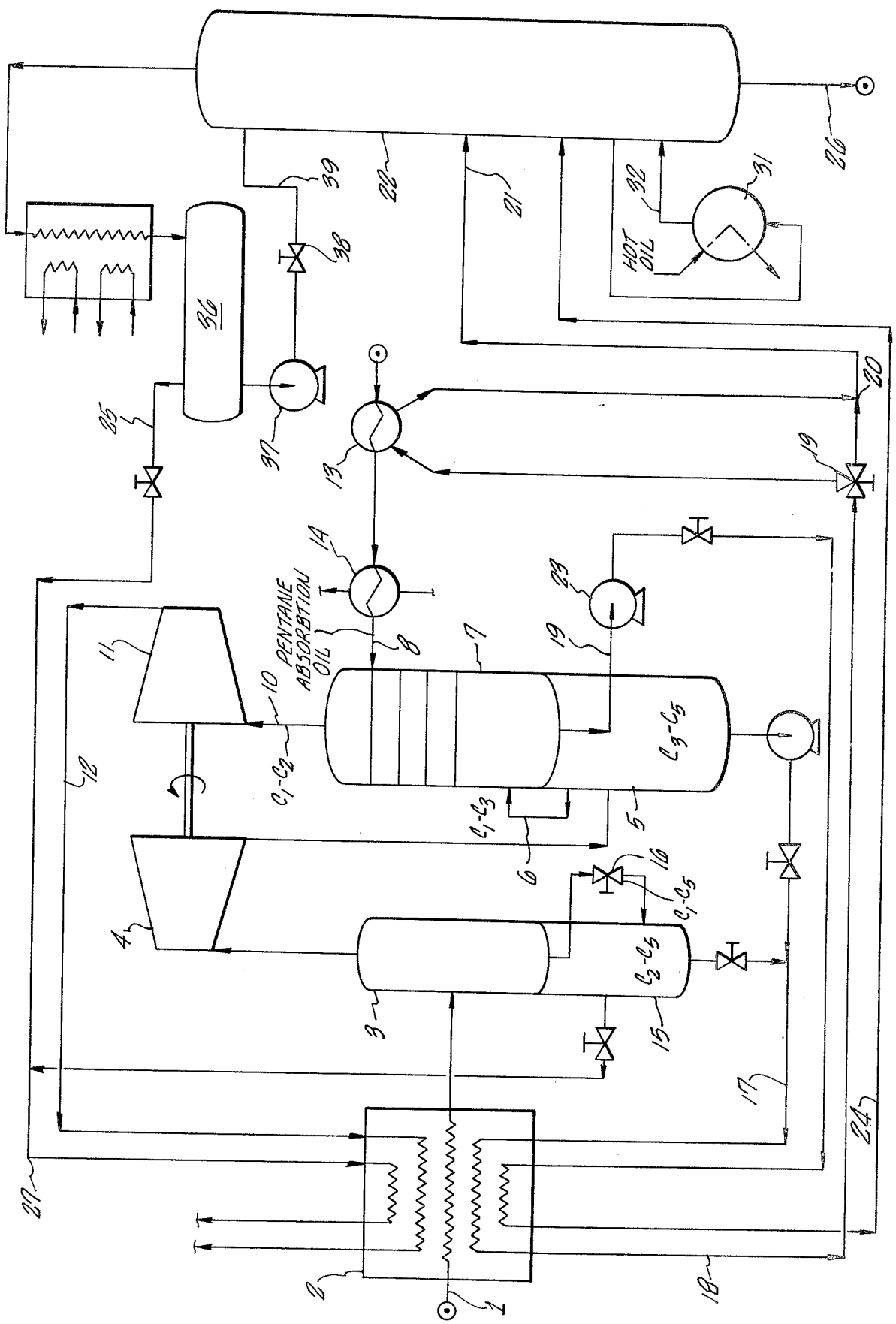

CRYOGENIC EXPANDER RECOVERY PROCESS

FIELD OF THE INVENTION

This invention relates to a process for treating a gaseous hydrocarbon containing feed stream such as natural gas or refinery gas to separate and recover $C_3$ and heavier components.

BACKGROUND OF THE INVENTION

Gaseous streams containing methane, ethane and heavier hydrocarbon components occur naturally, such as in natural gas, and also as by-products of a variety of refinery processes. These gases often contain, in addition to methane and ethane, a substantial quantity of hydrocarbons of higher molecular weight, as for example, propane, butane, and pentane and their unsaturated analogs. While it is frequently desirable or necessary for industrial purposes to retain the methane and ethane content in such gases, it is not necessary to retain the higher molecular weight hydrocarbons, and it is usually economically desirable to separate some or all of such components.

In present processing, propane and the heavier hydrocarbon components of natural gas and refinery gas are separated and recovered by liquification and cryogenic distillation at temperatures below 0° F. Refrigeration for separation is supplied totally or partially by expansion of the gaseous stream in a turboexpander which produces power that may be used, for example, in driving a compressor.

Prior to the advent of the cryogenic expansion process, such heavier component hydrocarbons were most frequently separated by liquification and treatment with an absorption medium. For example, natural gas streams containing propane and heavier hydrocarbon components were contacted with an absorption oil in which the liquids were absorbed and thereafter desorbed and recovered. However, with a cryogenic expansion process, it is practical to recover substantially higher percentages of the liquid hydrocarbons than with the absorption process; thus, using the cryogenic expansion process, in excess of eighty (80%) percent of the ethane content and over ninety (90%) percent of the propane and heavier components can be recovered economically. The use of absorption techniques for the separation and recovery of such hydrocarbon components therefore, is generally regarded as outdated and has fallen into disuse due to the clear economic advantages of cryogenic expansion.

In some cases, however, it is desirable to remove only part of the hydrocarbon components, as, for example, where there is no use for a particular component and, in the case of natural gas which may be unsatisfactory unless some of the heavier hydrocarbon components are retained. Specifically, ethane is often left in natural gas to increase the heating value of the natural gas and propane also may be intentionally left in the natural gas.

SUMMARY OF THE INVENTION

The present invention relates to those cases where it is desirable to leave substantially all of the ethane in the hydrocarbon gaseous stream and thus to separate and recover the $C_3$ and heavier hydrocarbon components. It has thus been found, unexpectedly, that increased percentages of such components can be economically recovered with the expenditure of less power by expanding the hydrocarbon gaseous feed stream in a cryogenic expansion step and subsequently contacting the expanded gas with an absorption medium. Such process has been found to be superior to both the cryogenic expansion process and the previously utilized absorption process.

The improved process of the present invention thus comprises partially condensing a gaseous hydrocarbon containing feed stream such as natural gas or refinery gas, thereby forming first vapor and liquid streams, which are then separated and the vapor stream expanded, cooled and partially condensed to form second vapor and liquid streams. The second vapor and liquid streams are separated, and the vapor stream is subjected to an absorption step in which propane and heavier hydrocarbons are liquefied and thereafter distilled and recovered as liquid product. The other constituents of the vapor stream, which includes the methane and ethane content, remain in vapor form and are subsequently compressed and recovered as product gas. The first liquid stream is partially vaporized and then subjected to a second separation step to produce further vapor and liquid streams, with the vapor stream recovered as gaseous product and the liquid stream combined with the liquid stream from the absorption step and passed to a distillation step whereby the propane and heavier hydrocarbons are separated and recovered as liquid product and the methane and ethane content remain in vapor form and are recovered as gaseous product.

BRIEF DESCRIPTION OF THE DRAWING

The FIGURE of drawing is a schematic diagram of a process according to the present invention.

DETAILED DESCRIPTION OF THE INVENTION

According to the present invention, a gaseous stream of natural gas or refinery gas which typically contains hydrocarbons of from 1 to 5 carbon atoms is processed to separate and recover the $C_3$ and heavier hydrocarbon components. As illustrated in the figure of drawing, the gaseous feed stream passes through incoming line 1 to heat exchanger 2 wherein it is cooled by indirect heat exchange and provides heat for several process streams as described more fully hereinafter. The gaseous feed stream is thus partially condensed within heat exchanger 2 to form a first vapor stream and liquid stream which are separated in separator 3. The first vapor stream, which has as its essential hydrocarbon content $C_1$ through $C_4$ hydrocarbons, is expanded in turboexpander 4 and thereby cooled and partially condensed to form second vapor and liquid streams which are separated in separator 5. The second vapor stream containing essentially $C_1$–$C_3$ hydrocarbons flows through line 6 to absorber 7 through which it flows upwardly contacting downwardly flowing absorption oil which enters through line 8. Prior to entering absorber 7, the absorption oil, which is essentially pentane, is first cooled by indirect heat exchange in 13 with a process stream as is described below and then further cooled by indirect heat exchange in 14 with a refrigerant.

Most of the $C_3$ content of the vapor stream entering absorber 7 through line 6 is absorbed into the absorption oil and leaves absorber 7 through line 9, where it is pressurized by pump 23, and flows back to heat exchanger 2, wherein it is warmed by receiving part of the heat given up by the incoming gaseous feed stream. The warmed propane rich oil then flows through line 24 and enters distillation column 22 at the lower portion thereof.

A third vapor stream consisting of the vapor constituents not absorbed into the absorption medium, i.e., essentially $C_1$ and $C_2$ hydrocarbons, exist the absorber 7 through line 10, and is compressed in compressor 11, which is driven by the power produced by turboexpander 4. The compressed vapor then flows through line 12 to heat exchanger 2 where it is warmed by heat from the incoming gaseous feed stream being cooled in heat exchanger 2. The warmed vapor is recovered as part of the product gas from the process. The $C_1$ and $C_2$ hydrocarbon contents may then be separated and recovered.

Referring again to the first liquid stream which is separated in separator 3, such stream, which contains $C_1$–$C_5$ hydrocarbons, flows to separator 15 via expansion valve 16 in which the pressure is reduced, resulting in a temperature drop and partial vaporization of the liquid to form a third vapor and liquid streams which are separated in separator 15. This third liquid stream contains $C_2$–$C_5$ hydrocarbons and is combined with the second liquid stream from separator 5 which contains $C_3$–$C_5$ hydrocarbons to form a fourth liquid stream which flows through line 17 to heat exchanger 2 in which it is warmed by passage in indirect heat exchange with the incoming gaseous feed stream. The warmed fourth liquid stream then flows through line 18 to control valve 19, where part of it is diverted to heat exchanger 13 where it cools the absorption oil passing to the absorption vessel. The diverted liquid stream is then recombined at 20 and flows to the distillation column 22.

In the distillation column 22, separation occurs such that the overhead product in line 25 contains substantially all of the methane and ethane in the incoming feed streams (lines 18 and 24) and only a very small amount of propane. Most of the propane and substantially all of the butane and pentane flow from distillation column 22 as a liquid bottom product in line 26. In the lower portion of column 22, the liquid $C_3$–$C_5$, which also contains some ethane, is removed through line 30 and is passed through reboiler 31 wherein the liquid is warmed by indirect heat exchange with hot pentane oil to be passed to the absorption column 7 as previously described. In passing through reboiler 31, the ethane content, along with some propane, is vaporized, and the vapor-liquid mixture is returned to column 22 through line 32, wherein the ethane and propane vapor pass upwardly through column 22 and exit as overhead product. The gaseous overhead stream passes through heat exchange unit 35 wherein the small portion of propane content present will condense, along with some ethane, and after passing through reflux drum 36, is pressurized by pump 37 and returned to column 22 as reflux by passing through control valve 38 and line 39.

The overhead product from line 25 is combined with the vapor stream in line 40 from the separator 15 and flows through line 27 to heat exchanger 2 in which it is warmed by heat exchange with the incoming gaseous feed stream. The warmed stream forms the remainder of the product gas from the process, and, along with the product gas coming through line 12 from compressor 11, is recompressed by compressors (not shown) for further process usage.

The liquid bottom product exiting column 22 through line 26 which contains the propane and heavier hydrocarbon components flows to further distillation columns that are not shown for separation into liquid products such as LPG, butane and pentane. Part of the pentane stream thus separated is recycled through reboiler 31 to absorber 7 as absorption oil.

The process of this invention will be further understood by reference to the following specific but illustrative example.

EXAMPLE

Propane and heavier natural gas liquids are recovered by the process of this invention from a natural gas stream having the following composition:

|  | Pounds Per Hour |
| --- | --- |
| $CH_4$ | 439,470 |
| $C_2H_6$ | 57,890 |
| $C_3H_8$ | 21,140 |
| $C_4H_{10}$ | 12,569 |
| $C_5H_{12}$ | 2,180 |
|  | 533,240 |

Natural gas enters through line 1 at a temperature of 95° F. and a pressure of 837 psia. It is cooled to a temperature of −65° F. in exchanger 2 by indirect heat exchange and partially condensed, forming a first vapor stream and a first liquid stream, which are separated in 3. The first vapor stream is expanded in turboexpander 4 to a pressure of 475 psia, thereby generating 2145 shaft horsepower. During the expansion, the stream is cooled to −107° F. and partially condensed forming second vapor and second liquid streams which are separated in 5. The second vapor stream flows through line 6 and into absorber 7, where the temperature is −103° F. and the pressure is 475 psia, and flows upwardly through the absorber, contacting downflowing absorption oil which enters 7 through line 8. The absorption oil is first cooled by indirect heat exchange in 13 with a process stream as described below and is further cooled by indirect heat exchange in 14 with a refrigerant to −45° F. before entering absorber 7. Most of the propane which enters the absorber through line 6 is asorbed in the oil and leaves through line 9. A third vapor stream exits absorber 7 through line 10 at a pressure of 474 psia and a temperature of −97° F. and is compressed in compressor 11 to 621 psia, using the horsepower supplied by turboexpander 4. The compressed vapor at a temperature of −65° F. flows through line 12 to exchanger 2 where it is warmed to 80° F. by indirect heat exchange with the incoming natural gas feedstream. The warmed vapor is part of the product gas from the plant.

The first liquid stream which is separated in 3 flows to separator 15 via expansion valve 16 where the pressure is reduced to 520 psia resulting in a temperature drop to −90° F. and partial vaporization of the stream, forming third vapor and liquid streams which are separated in 15. The third liquid stream is combined with the second liquid steam from separator 5, forming a fourth liquid stream which flows through line 17 at a temperature of −100° F. to exchanger 2 where it is warmed to 40° F. The warmed fourth liquid stream flows through line 18 to control valve 19 where part of the stream is diverted to exchanger 13 where it cools the absorption oil to 36° F. as previously described. The diverted stream is recombined at 20 and flows to a middle feed point of distillation column 22 at a temperature of 45° F.

Propane rich oil in line 9 is pressurized by pump 23 and flows to heat exchanger 2 where it is warmed to 80°

F. The warmed rich oil flows through line 24 to the lower feed point of 22.

The overhead product from column 22 is combined with the third vapor stream from separator 15 and the combined stream flows through line 27 to exchanger 2 where it is warmed to 80° F. by receiving the remainder of the heat given up by the incoming natural gas. The warmed stream forms the remainder of the product gas from the plant. The two streams of product gas are recompressed to the starting pressure of 837 psia.

Within distillation column 22, the temperature in the lower portion is 246° F. and the pressure is 500 psia. In the upper portion, the temperature is −7° F. and the pressure is 495 psia. The overhead stream enters heat exchanger 35 at a temperature of −7° F. and is cooled to −42° F. Liquid $C_3$ and higher hydrocarbons are removed from column 22 at a temperature of 246° F.

Table 1 gives a comparison of the performance of the process of this invention with a conventional cryogenic-/expansion process.

TABLE 1

|  | New Process | Conventional Cryogenic/Expansion Process |
|---|---|---|
| Feed Gas - MM SCFD | 274 | 274 |
| Products - #/Hr |  |  |
| Propane | 19,660 | 19,040 |
| Butane | 12,551 | 12,412 |
| Pentane | 1,664 | 2,170 |
| Net Residue Gas - MM SCFD (after deducting fuel for power) | 266 | 265 |
| Horsepower Input (for refrigeration and recompression) | 8,500 | 11,100 |

Not only is substantially more propane recovered by the process of this invention, but less fuel is required because less horsepower is used to recompress the residue gas. Furthermore, the fact that less horsepower is required, means that less compression equipment must be purchased and the capital cost would thus be approximately $1,000,000 less for the process of this invention. Although the distillation equipment associated with the process of this invention would be somewhat larger than for the conventional cryogenic/expansion process because the absorption oil must be recycled through such equipment, this is a relatively minor economic factor.

The foregoing description has been directed to a presently preferred embodiment of the process of this invention. It will be appreciated, however, by those skilled in the art that variations in the described process may be made within the scope of the invention, and the process accordingly is to be limited only by the lawful scope of the claims which follow.

We claim:

1. A process for the recovery of hydrocarbons from a gaseous hydrocarbon containing feedstream comprising:

(1) partially condensing such feedstream to form first vapor and liquid streams, (2) separating said vapor and liquid streams and expanding said separated vapor stream, thereby cooling and partially condensing the same to form second vapor and liquid streams, (3) separating said second vapor and liquid streams and subjecting said second vapor stream to an absorption step, whereby propane and heavier hydrocarbons from said second vapor stream are absorbed from said vapor, and are thereafter distilled and recovered as liquid product, with the other constituents of said second vapor stream remaining in vapor form and subsequently being recovered as product gas, (4) passing said first liquid stream to a second separation step, thereby producing additional vapor and liquid streams, (5) combining said liquid stream from step (4) with said second liquid stream and passing the combined stream to a distillation step, whereby methane and ethane are recovered therefrom as gaseous product, and said vapor stream from step (4) being thereafter combined with said gaseous product from said distillation step and recovered as gaseous product.

2. The process of claim 1 in which the constituents of said second vapor stream remaining in vapor form after said absorption step are compressed prior to recovery, utilizing the power produced by said expansion step.

3. The process of claim 1 in which said gaseous feed stream is natural gas or refinery gas.

4. The process of claim 1 in which said stream of absorbed propane and heavier hydrocarbons is passed in indirect heat exchange with said gaseous feed stream prior to distillation.

5. The process of claim 1 in which the absorption medium is butane, pentane, or heavier hydrocarbons.

6. The process of claim 1 in which said first vapor stream contains as its essential hydrocarbon content primarily $C_1$–$C_4$ hydrocarbons and said first liquid stream contains $C_1$–$C_5$ hydrocarbon components.

7. The process of claim 1 in which said second vapor stream contains as its essential hydrocarbon component primarily $C_1$–$C_3$ hydrocarbons and said second liquid stream contains $C_3$–$C_5$.

8. The process of claim 1 in which the vapor stream remaining after said absorption contains as its essential hydrocarbon content primarily $C_1$ and $C_2$ hydrocarbon.

9. The process of claim 1 in which the liquid stream resulting from separation of step 4 contains as its essential hydrocarbon content $C_2$–$C_5$ hydrocarbons.

10. A process for the recovery of hydrocarbons from a gaseous hydrocarbon containing feed stream of natural gas or refinery gas comprising:

(1) partially condensing such feed stream to form first vapor and liquid streams, said vapor stream containing as its essential hydrocarbon content $C_1$–$C_4$ hydrocarbons and said liquid stream containing $C_1$–$C_5$ hydrocarbon components, (2) separating said vapor and liquid streams and expanding said separated vapor stream, thereby cooling and partially condensing the same, to form second vapor and liquid streams, said second vapor stream containing as its essential hydrocarbon content $C_1$–$C_3$ hydrocarbons and said liquid stream containing $C_3$–$C_5$ hydrocarbons components, (3) separating said second vapor and liquid streams and subjecting said second vapor stream to an absorption step, whereby $C_3$ and heavier hydrocarbons from said second vapor stream are absorbed from said vapor into the absorption medium, and are thereafter distilled and recovered as liquid product, with the other constituents of said second vapor stream remaining as vapor and thus forming a third vapor stream which is subsequently recovered as a product gas, said third vapor stream containing as its essential hydrocarbon content primarily $C_1$ and $C_2$ hydrocarbons,
(4) passing said first liquid stream to a second separation step, thereby producing additional vapor and liquid streams, said vapor stream containing as its essential hydrocarbon content primarily $C_1$ and $C_2$ hydrocarbons and said liquid stream containing $C_2$-$C_5$ hydrocarbon components,
(5) combining said liquid stream from step 4 with said second liquid stream and passing the combined stream to a distillation step, whereby methane and ethane are combined therefrom as gaseous product, and
(6) said vapor stream from step 4 being combined with said gaseous product from said distillation and recovered as gaseous product.

11. The process of claim 10 in which said third vapor stream is compressed prior to recovery, utilizing the power produced by said expansion step.

12. A process for the recovery of hydrocarbons from a gaseous hydrocarbon containing feedstream comprising:
(1) partially condensing such feedstream to form first vapor and liquid streams,
(2) separating said vapor and liquid streams and expanding said separated vapor stream, thereby cooling and partially condensing the same to form second vapor and liquid streams,
(3) separating said second vapor and liquid streams and subjecting said second vapor stream to an absorption step, whereby ethane and heavier hydrocarbons from said second vapor stream are absorbed from said vapor, and are thereafter distilled and recovered as liquid product, with the other constituents of said second vapor stream remaining in vapor form and subsequently being recovered as product gas,
(4) passing said first liquid stream to a second separation step, thereby producing additional vapor and liquid streams,
(5) combining said liquid stream from step (4) with said second liquid stream and passing the combined stream to a distillation step, whereby methane is recovered therefrom as gaseous product, and said vapor stream from step (4) being thereafter combined with said gaseous product from said distillation step and recovered as gaseous product.

* * * * *